United States Patent [19]

Goldberg et al.

[11] Patent Number: 5,019,059
[45] Date of Patent: May 28, 1991

[54] APPARATUS AND METHOD FOR COLLECTING BODY FLUIDS

[75] Inventors: Edward M. Goldberg, Glencoe; Lev Melinyshyn, Mt. Prospect, both of Ill.

[73] Assignee: Uresil Corporation, Skokie, Ill.

[21] Appl. No.: 228,935

[22] Filed: Aug. 2, 1988

Related U.S. Application Data

[63] Continuation-in-part of Ser. No. 941,769, Dec. 15, 1986, abandoned.

[51] Int. Cl.$^5$ .............................................. A61M 1/00
[52] U.S. Cl. ................................................... 604/317
[58] Field of Search ............................... 604/317–321, 604/323–325, 128, 133, 118, 119; 128/DIG. 24

[56] References Cited

U.S. PATENT DOCUMENTS

| D. 262,657 | 1/1982 | Ekbladh | D24/4 |
| 2,397,257 | 3/1946 | Goland et al. | |
| 2,759,477 | 8/1956 | Mains | |
| 2,795,245 | 6/1957 | Meehan | 141/26 |
| 3,115,138 | 12/1963 | McElvenny et al. | |
| 3,421,504 | 1/1969 | Gibbons | |
| 3,463,159 | 8/1969 | Heimlich | |
| 3,742,952 | 7/1973 | Magers et al. | |
| 3,774,611 | 11/1973 | Tussey et al. | |
| 3,779,243 | 12/1973 | Tussey et al. | |
| 4,278,089 | 7/1981 | Huck et al. | |
| 4,435,171 | 3/1984 | Goldberg et al. | 604/49 |
| 4,439,190 | 3/1984 | Protzmann et al. | 604/319 |
| 4,512,771 | 4/1985 | Norton | 604/333 |
| 4,529,402 | 7/1985 | Weilbacher et al. | 604/133 |
| 4,781,707 | 11/1988 | Boehringer et al. | 604/317 |

FOREIGN PATENT DOCUMENTS 1304324 1/1973 United Kingdom.

Primary Examiner—David J. Isabella
Attorney, Agent, or Firm—Barry W. Sufrin

[57] ABSTRACT

A truly closed drainage apparatus for suctioning, storing and administering fluid from body and tissue cavities including draining means for suctioning and receiving fluid, a reservoir for siphoning and storing excess fluids, a small pore hydrophobic filter for venting air without retrograde introduction of microorganisms, and means for applying pressure to the reservoir to administer the fluid contained therein.

10 Claims, 3 Drawing Sheets

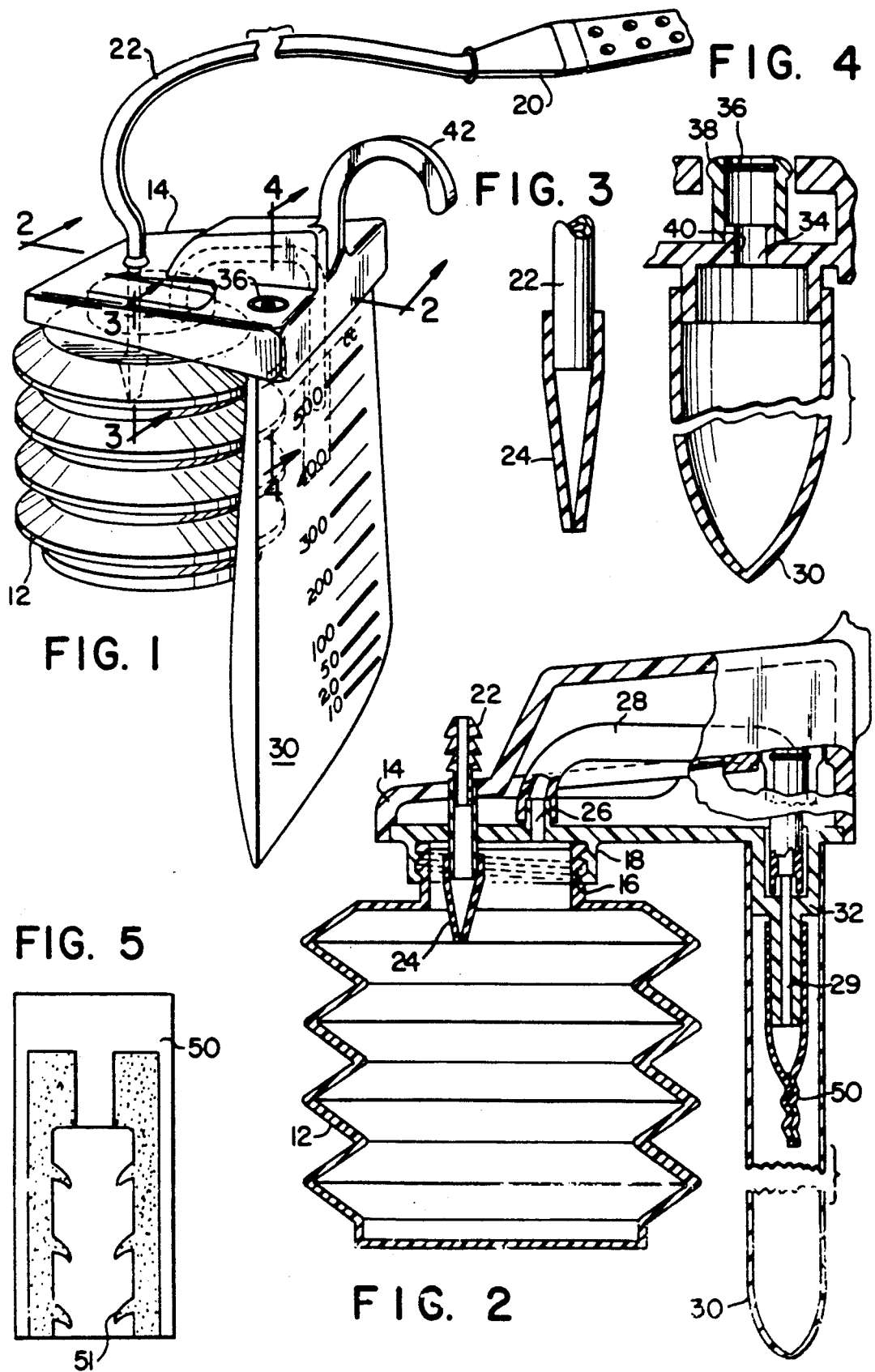

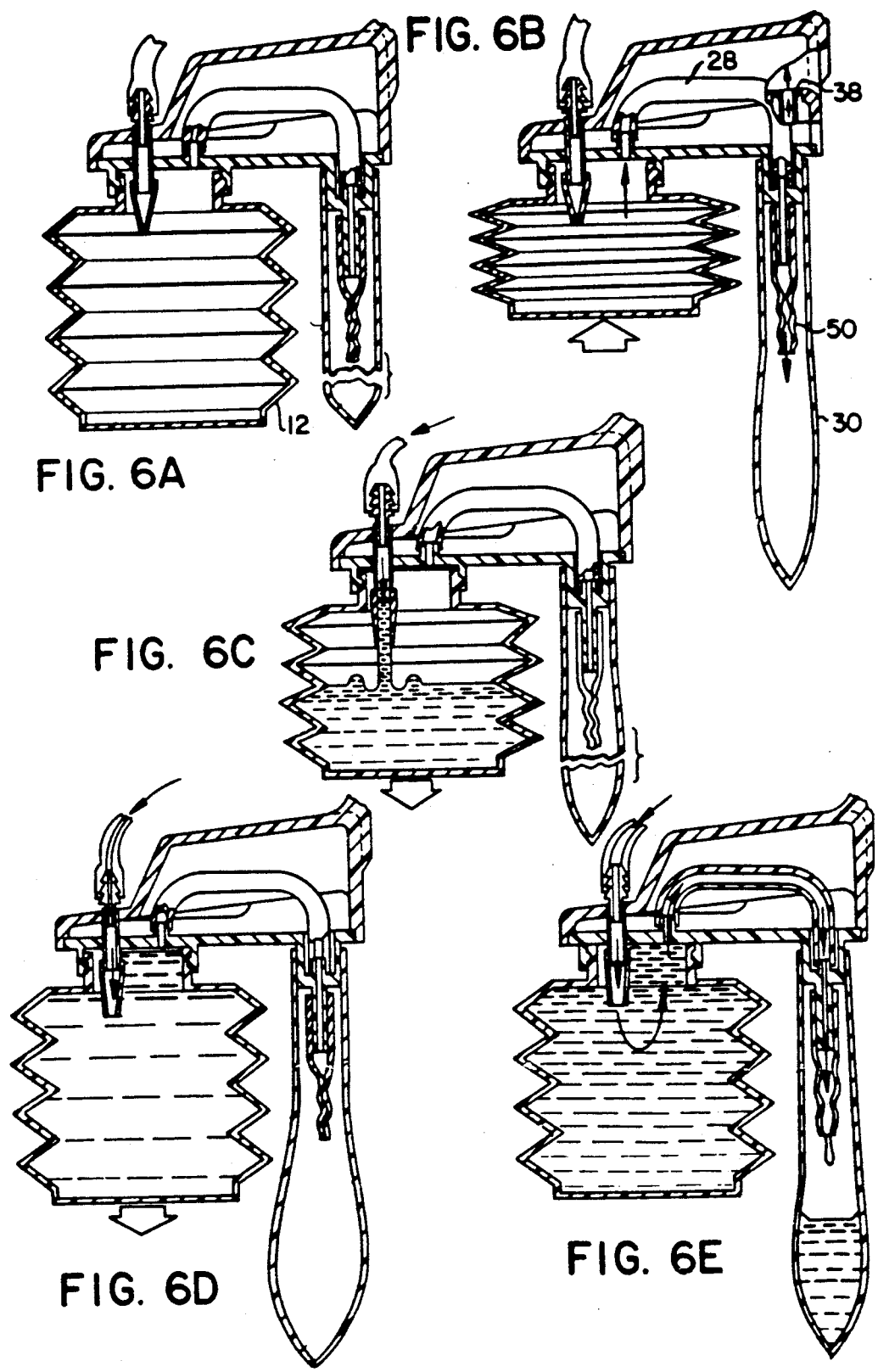

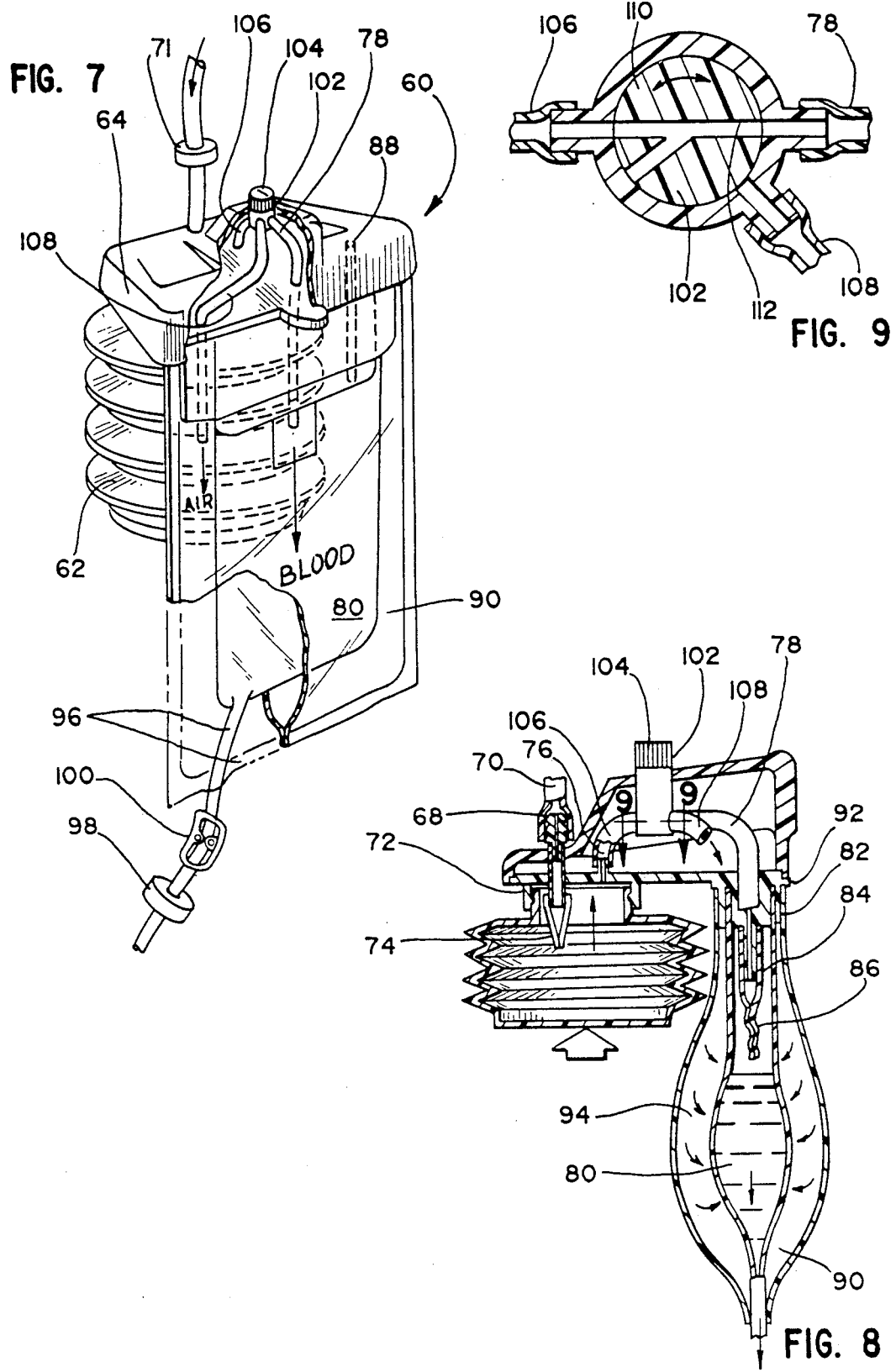

APPARATUS AND METHOD FOR COLLECTING BODY FLUIDS

This application is a continuation-in-part of previously filed application, Ser. No. 941,769, filed Dec. 15, 1986, now abandoned.

BACKGROUND OF THE INVENTION

This invention relates generally to apparatus and methods for suctioning body fluids. More particularly, it relates to apparatus and methods for reducing the likelihood of contamination and infection during the collection of fluids from body cavities of human and animal subjects by suctioning fluids and disposing of or reusing those fluids without exposing the apparatus, the subjects or the collected fluids to potential sources of contamination and infection.

In modern medical practice it is often necessary or desirable to initiate drainage from body cavities in patients and to collect and contain these body fluids. In such situations, it is essential to prevent undesirable microorganisms from gaining access to both the drained cavity and to the collecting reservoir. It is also necessary to prevent undesirable microorganisms from gaining access to the collected fluids when those fluids are to be reused rather than discarded. By enclosing and preventing contamination of the collecting reservoir, the likelihood of retrograde contamination of the patient and cross contamination of the patients and hospital personnel is greatly reduced.

Unfortunately, conventional, commercially available, drainage devices are a prime source of infection in catheterized patients. For example, in the area of bladder drainage, a large proportion of catheterized patients suffer from urinary tract infections attributable to contaminated drainage devices. In most cases, the drainage collection device itself becomes contaminated in use and infection then ascends in a retrograde manner from the drainage collection device to the patient via the drainage catheter. Such retrograde infection from contaminated drainage or infusion devices has been observed, for example, in patients undergoing urinary, wound, biliary, gastro-intestinal drainage, peritoneal dialysis, and hyperalimentation treatment. See, e.g. E. M. Goldberg, et al., "Peritoneal Dialysis", *Dialysis and Transplantation*, June/July 1975, Vol. 4 #4; J. H. Isaccs, et al., "Foley Catheter Drainage Systems and Bladder Damage", *Surgery, Gynecology & Obstetrics*, May 1971, p.889; R. E. Desautels, "The Causes of Catheter-Induced Urinary Infections and Their Prevention", *J. Urology*, 1969, 101:757: R. E. Desautels, et al. "Technical Advances in the Prevention of Urinary Tract Infection", *J. Urology*, 1962, 87:487; R. E. Desautels, "Aseptic Management of Catheter Drainage", *New Eng. J. Med.*, 1960, 263:189; E. H. Kass, et al., "Prevention of Infection of Urinary Tract in Presence of Indwelling Catheters", *J.A.M.A.* 1959, 169:1181; and E. H. Kass, et al. "Entry of Bacteria into the Urinary Tracts of Patients with Inlying Catheters" *New Eng. J. Med.*, 1957, 256:556.

Contamination of drainage collection devices often arises from containers or reservoirs designed to be filled repeatedly with drained body fluid and regularly emptied so suction can be resumed. For example, the evacuator described by McElhenny in U.S. Pat. No. 3,115,138 includes a capped fluid outlet. After the evacuator becomes filled it is emptied for reuse by removing the cap and expelling collected fluid via the outlet. During this operation the interior of the evacuator is exposed to the atmosphere and contamination of the evacuator will result.

Efforts have been made to reduce the contamination of drainage devices during periodic emptying. For example, U.S. Pat. Nos. 3,779,243 and 3,774,611 disclose evacuators which employ a special valve over the fluid outlet. This valve operates to close the outlet at all times except for the time when fluid is actually being purged from the evacuator. Such evacuators may succeed in reducing the contamination brought on by purging. However, since these evacuators must be periodically opened for purging, they are exposed to the surrounding atmosphere and will become contaminated and therefore a potential source of infection.

U.S. Pat. No. 4,435,171 for Apparatus to Be Worn And Method For Removing Fluid From A Living Subject, describes a closed, gravity drainage system designed to minimize retrograde introduction of microorganisms into a patient. This system, however, has no provision for suction drainage.

U.S. Pat. No. 4,265,243 describes one very complex liquid collection receptacle assembly in which urine is drained from a patient's bladder under the force of gravity into an intermediate collection chamber from which it is emptied into a larger receptacle either by siphoning or by squeezing the first chamber to force the urine from it. This apparatus, unfortunately, is most complex, and, as a gravity system, lacks the ability to suction fluid from the bladder or any other body cavity.

To the best of the present inventor's knowledge, no commercially available so-called "closed drainage" system is a "truly" closed drainage system. All current commercially available drainage systems were originally developed to avoid open drainage by enclosing the drainage through the catheter into a receptacle. The receptacle in all such systems is periodically emptied, opening the system up to potential contamination.

In modern medical practice, it is often desirable to efficiently collect blood, gastric, biliary, pancreatic, small bowel (succus entericus) and other bodily fluids into safe, economical containers, so that the fluids can be reused and returned if and when needed. In fact, with the widespread concern such diseases as acquired immune deficiency syndrome, which can be transmitted by the transfer of bodily fluids, it is particularly desirable to be able to collect blood from an individual, filter that blood as necessary to remove clots, particles, foreign bodies and microorganisms and then either store or immediately return the blood to that individual. Whether or not the collected fluids are to be administered to the patient from whence they came or to another patient, it remains essential to prevent contamination and infection from reaching the collected fluid.

SUMMARY OF THE INVENTION

The present invention comprises a truly closed drainage apparatus for receiving fluid (liquids and gases) from body and tissue cavities including suctioning means in communication with the cavities for suctioning and receiving the drained body fluids. The present invention also comprises a truly closed drainage apparatus for receiving fluid from body and tissue cavities in which the collected fluids are maintained in an uncontaminated state and reused from the container into which they were originally collected.

In one important embodiment of the invention, the suctioning means comprise a resilient bellow which draws body fluid from the cavities under the inherent spring back suction force produced as it returns to its normal, expanded condition. When the collected fluids are to be reused in the "transfusion" configuration of the invention, the bellows also provides pressure for driving the collected fluid out of apparatus.

The apparatus includes a reservoir into which excess body liquids from the suctioning means are automatically siphoned and into which the suctioning means may be emptied, all without exposure of the system to the ambient atmosphere. In an important embodiment of the invention, the reservoir consists of an impervious, flexible bag in communication with an outlet port of the suctioning means which has a one-way valve at its inlet to prevent liquid from flowing back from the reservoir. When the collected fluids are to be reused, either immediately or after storage for a period of time, an impervious, flexible outer pressure bag is provided for driving the fluids collected in from the secondary reservoir into a patient, as needed.

Yet another important embodiment of the invention, the reservoir is vented to the atmosphere through one or more small pore hydrophobic filters to permit gases in the system to be purged without retrograde introduction of microorganisms into the reservoir.

It is therefore an object of the present invention to provide an improved apparatus and method for draining body fluids from a body cavity under suction in which potential retrograde infection due to contamination of drainage devices from exposure to the ambient atmosphere is eliminated.

It is a further object of the present invention to provide an improved apparatus and method for collecting body fluids including liquids and gases from a body cavity under suction in which collected liquids are siphoned into disposable containers for disposal and collected gases are vented to the atmosphere without exposing the system to the atmosphere and without exposure and contamination of hospital personnel from the container contents.

Yet another object of the invention is to provide a closed drainage system in which gases in the system can be purged without exposing the system to the ambient atmosphere.

A still further object of the present invention is to provide an economical, easy to use, truly closed suction drainage apparatus and method.

Another object of the present invention is to provide an economical, easy to use and safe apparatus for collecting blood and other bodily fluids and administering the blood and other fluids either to the donor or to another party, without requiring additional containers or special apparatus.

A still further object of the present invention is to provide an apparatus for collecting blood and other bodily fluids, filtering those fluids as necesssary, and immediately administering the fluids under pressure to the patient.

These and other objects of the present invention will become apparent to those skilled in the art upon consideration of the accompanying specification, claims and drawings.

BRIEF DESCRIPTION OF THE DRAWINGS

The features of this invention which are believed to be novel are set forth with particularity in the appended claims. The invention, together with its objects and advantages, may be best understood by reference to the following description, taken in conjunction with the following drawings, in which like reference numerals identify like elements in the several figures and in which:

FIG. 1 is a perspective view of a closed drainage apparatus in accordance with the practice of the present invention;

FIG. 2 is a cross-sectional elevation view of the apparatus of FIG. 1, taken generally along section line 2—2 of that figure;

FIG. 3 is an enlarged cross-sectional view of a one-way valve illustrated in FIG. 1, taken along section 3—3 of FIG. 1;

FIG. 4 is an enlarged cross-sectional view of that portion of the apparatus of FIG. 1 containing a vent hole and filter for purging air from the apparatus, taken along section line 4—4 of FIG. 1;

FIGS. 6A-6E are cross-sectional elevation views of the apparatus of FIG. 1, showing the operation of the apparatus of FIG. 1 in draining and storing body fluids;

FIG. 7 is a perspective view of an apparatus of the invention adapted for receiving fluids and subsequently administering those fluids;

FIG. 8 is an elevation cross-sectional view of FIG. 7; and

FIG. 9 is a side cross-sectional elevation view of a control of the apparatus of FIG. 7 taken along lines 9—9 of FIG. 7.

DESCRIPTION OF THE PREFERRED EMBODIMENT

Turning now to FIGS. 1 and 2, an apparatus for collecting body fluids 10 is illustrated including a resilient bellows 12 mounted to a support housing 14 by way of an externally threaded neck 16 which is screwed into an internally threaded integral flange 18 of the housing. In an alternative embodiment, the bellows is permanently and sealingly affixed to the housing to prevent accidental opening of the system at the bellows-to-housing interface.

The bellows, which serves as the suctioning means of the invention as well as, as a pressure source, is preferably constructed of polyethylene, although it may be made of other impervious resilient materials such as polypropylene. In fact, the suctioning may be accomplished using any sort of reservoir capable of producing sufficient negative pressure, when evacuated, to draw blood, bile, serum, pus, gases and other fluids from a wound site. In the illustrated embodiment, resilient bellows 12 has a liquid capacity in its normal extended state of about 150 cc.

A conventional drain 20 of the type placed in body or tissue cavities of patients undergoing urinary, wound, biliary, gastro-intestinal drainage, peritoneal dialysis, and hyperalimentation treatment is connected to a suction port 22 of the apparatus by way of an appropriate length of flexible tubing 24 affixed at one end to the drain and at the other end to the proximal end of the suction port.

Suction port 22 passes through housing 14 and into the area circumscribed by flange 18. A one-way gross reflux valve 24 (FIG. 3) is affixed to the distal end of the suction port, positioned as near as practical to the top of bellows 12. Although it is preferred that a duckbill valve be used as the gross reflux valve, other conventional one-way valves may be used, such as ball, check and diaphragm valves. The primary consideration in the choice of the valve is that it prevent fluid reflux and that it not interfere with the bellows when the bellows is compressed during operation of the apparatus.

In addition to suction port 22, a drainage port 26 passes through housing 14 and into the area circumscribed by flange 18 to communicate with the interior of bellows 12. The distal end of the drainage port is connected to a conduit 28 interconnecting the suctioning means and the reservoir which is supported in the housing (FIG. 2A) to maintain the suctioning and reservoir means in fluid communication at all times. In the illustrated embodiment, reservoir 30 is a clear, flexible polyethylene bag although other impervious containers (flexible or rigid) could be used. The size of the reservoir is a matter of choice, although in typical applications where a polyethylene bag is used, the reservoir will be large enough to the contain 500, 1000, or 2000 cc of liquid. As illustrated in the figures, reservoir 30 has a 500 cc capacity and is marked to indicate its level of fill.

Reservoir 30 is attached and heat sealed to a flange 32 protruding downwardly from housing 14. A rigid tube 29 protrudes from the flange into the top of reservoir 30 where it terminates in a second anti-reflux valve 50.

Anti-reflux valve 50 must be chosen for maximum contact sealing area to prevent blood clots and other solids from causing leakage across the valve. While a conventional Heimlich valve could be used, a film valve 50 particularly useful in this application is illustrated in FIG. 5. In addition to its excellent sealing properties (even in the presence of solids in the sealing area), the film valve is particularly well adapted to the present application since it does not create dead space in reservoir 30.

The film valve is made up of two pieces of virtually any type of plastic film, such as polyethylene, mylar, nylon or PVC, as well as laminates of these materials. The only requirement in choosing the plastic films is that the combination of plastics do not adhere. Also, it has been found to be preferable to use films with a combined thickness in the range of about 3-5 mils. The edges of the two film members of the valve are heat sealed to each other with a tortuous profile 51 at the closed edges of the valve in order to prevent fluid leakage.

Housing 14 includes a vent 34 (FIG. 4) in communication with reservoir 30. Vent 34 permits air from the reservoir to escape as it is filled with liquid during the drainage procedure. The vent also permits gases which may be drawn into the system from the drain site by way of drain 20 to escape. Absent vent 34, reservoir 30 would not be able to be filled to capacity with liquid due to space taken up by gases in the system. Also, by eliminating gases from the system through vent 34, the reservoir may be maintained in a lower and easier to handle profile.

A small pore hydrophobic filter 36 is heat sealed into vent cup 34 which is friction fit onto a flange 40 encircling port 34. Filter 36 prevents the migration of bacteria into the system. It also makes it possible to vent gases without impairing the "closed" nature of the system. The vent cap is positioned at the top of the housing in order to prevent the filter from getting wet, which could cause clogging. Although only a single vent cup and filter are illustrated in order to simplify the figures, two or more cups and filters could be used.

Hydrophobic filter 36 must have a pore size less than or equal to 0.45 microns in order to prevent bacterial migration. One useful filter material is an expanded PTFE membrane available from W. L. Gore & Associates, Inc. of Elkton, Md. under the name "GORE-TEX EXPANDED PTFE". Alternative materials include woven fabric filters such as those available from PALL Bio-Medical Products Corporation of Glencove, N.Y. under the trademark "PALLFLEX".

The operation of the above apparatus of the present invention is illustrated in FIGS. 6A-E. It is to be understood in this discussion of the operation of the apparatus of the invention that the apparatus is affixed to the patient's bed or clothing by way of hook 42 (FIG. 1) or other fastening devices at a position below the wound site.

Looking first to FIG. 6A, the apparatus is shown in an empty condition, with bellows 12 extended. In FIG. 6B the bellows are manually compressed, forcing the air in the bellows through tube 28, past valve 50 and out of the system through hydrophobic filter 34.

In FIG. 6C, the resilient bellows are permitted to expand. Since the system is sealed (film valve 50 is closed due to the suction created by the bellows), liquid and gases are drawn from the wound site through the suction port 22 past gross reflux valve 24 and into the bellows.

One started, the bellows continue filling with fluid (FIG. 6D) until the liquid reaches the bellows top. At that point, due to the siphon effect produced by the positioning of the apparatus below the wound site, surplus liquid automatically enters tube 28 and flows into reservoir 30, as shown in FIG. 6E. The fluid entering the bag displaces any gases therein which exit the system through vent 34 and filter 36.

Turning now to FIGS. 7-9, there is illustrated an apparatus 60 in accordance with the present invention for collecting and administering body fluids, which includes a resilient bellows 62 sealingly mounted to a support housing 64. The bellows, which comprises the source both of suction and pressure for the apparatus, is described above in connection with the embodiment of FIGS. 1-6.

A conventional drain of the type illustrated at 20 in FIG. 1 is connected to the suction port 68 of the apparatus by way of an appropriate length of flexible tubing 70 affixed at one end to the drain and at the other end to the suction port. In addition, in the embodiment illustrated, the apparatus is adapted for collecting blood and an in-line blood clot filter 71 is therefore mounted in tubing 70 ahead of the inlet port. When other materials are collected, appropriate conventional filtering media will be used.

Suction port 68 passes through housing 64 and into the area circumscribed by flange 72. A one-way gross reflex valve 74 is affixed to the suction port and positioned as described above in connection with FIG. 3.

A drainage port 76 passes through housing 64 and into the areas circumscribed by flange 72 to communicate with the interior of the bellows. The distal end of the drainage port is connected to a tube 78, located within the housing, which is routed to the top of a reservoir 80. This reservoir is a flexible bag of the type described above in connection with the discussion of reservoir 30 of FIGS. 1-6. As also described there, reservoir 80 is attached and heat sealed to a flange 82 which protrudes downwardly from the housing.

A rigid tube 84 protrudes from the flange into the top of reservoir 80 where it terminates in a second anti-reflux valve 86. Again, the anti-reflux valve is as described above in connection with the discussion of antireflux valve 50 of the device of FIGS. 1-6. In addition, housing 64 includes a vent 88 in communication with reservoir 80. This vent functions in the same fashion as vent 34, discussed above.

The apparatus of FIGS. 7-9 also includes an outer pressure bag, 90, sealingly affixed to flange 92. The pressure bag is larger than the blood bag and completely circumscribes it. This establishes an airtight pressure interface 94 surrounding reservoir 80.

An administration tube 96, which is sealingly affixed to reservoir 80, crosses the pressure interface and protrudes beyond the edge 96 of the pressure bag. The pressure bag is sealed about the administration tube at 96 to maintain the airtight condition of the pressure interface. Another filter 98 is positioned on the administration tube to further filter the blood being administered to the patient. In addition, a conventional bubble trap (not shown) can be placed in line, preferably after the filter, to remove air bubbles from the blood. A clamp 100 or other device closes off the administration tube when not in use.

Finally, the apparatus includes a control 102 which diverts air expelled from bellows 62 either to reservoir 80 (from which it escapes to the atmosphere through hydrophobic filter 88) or to the pressure interface 96. The operation of control 102 can best be understood by an examination of FIGS. 7 and 9.

In FIG. 7, three tubes, 78, 106 and 108 are illustrated, communicating respectively with reservoir 80, bellows 62 and pressure interface 94. Valve 102 is provided with a "Y" shaped passage 110 in which the bellows can be placed in communication through tube 106 respectively with reservoir 80 (by way of tube 78) or pressure interface 94 (by way of tube 108) by simply rotating the control stem 104 to align leg 112 of the passage with either tube 78 or 108.

The apparatus illustrated in FIGS. 7-9 is used in collecting and administering blood as follows:

1. Bellows 62 are manually compressed, forcing the air in the bellows through tube 78, across control 102 and into reservoir 80 from which it escapes to the atmosphere through hydrophobic filter 88;

2. The resilient bellows are permitted to expand, drawing blood from the patient, through filter 71 and into the bellows.

3. The bellows are compressed, driving the blood out of the bellows through tube 78 across control 102 and into reservoir 80. The bellows are allowed to expand again, drawing further blood from the patient through the gross filter and into the bellows.

4. The above process is repeated until the reservoir is filled, or the blood is needed.

5. When it is desired to administer the blood contained in the reservoir, control 102 is turned to divert air from the bellows through tube 108 into pressure interface 94. Bellows 62 are repeatedly compressed, building up the pressure in the pressure interface, creating a "pressure cuff" which squeezes the inner bag (FIG. 9).

6. Administration tube 96 is attached to a cannula or other appropriate device for administration of the blood to a patient, and with the device connected to the patient, clamp 100 is opened to permit the blood in the reservoir to rapidly flow to the patient under the pressure of the air contained in the pressure interface.

While particular embodiments of the invention have been shown and described, it will be obvious to those skilled in the art that various changes and modifications may be made therein without departing from the spirit and scope of the invention and, therefore, it is intended in the appended claims to cover all such changes and modifications which fall within the true spirit and scope of the invention.

What is claimed is:

1. A closed drainage apparatus for collecting and administering to a patient liquids suctioned from body and tissue cavities comprising:
    suctioning means, in communication with the body and tissue cavities, for suctioning and receiving liquids and gases from the cavities, said suctioning means comprising a resilient container which is compressible to create a suctioning force as it returns to its normal expanded condition;
    reservoir means, for receiving and storing excess liquids from said suctioning means;
    a conduit, in communication with said reservoir, for transporting liquids from said reservoir to the patient; and
    means, circumscribing said reservoir means, for applying pressure to said reservoir means to drive the collected fluids from said reservoir means through said conduit, said pressure applying means comprising an impervious flexible bag which circumscribes said reservoir means to establish an airtight pressure interface in the space between the outside wall of said reservoir means and the inside wall of said container, and means for inflating said airtight pressure interface.

2. The closed drainage apparatus of claim 1 wherein said suctioning means serves as well as said inflating means.

3. A closed drainage apparatus for collecting and administering to a patient liquids suctioned from body and tissue cavities comprising:
    suctioning means, in communication with the body and tissue cavities, for suctioning and receiving liquids and gases from the cavities;
    reservoir means, for receiving and storing excess liquids from said suctioning means;
    a conduit, in communication with said reservoir means, for transporting liquids from said reservoir to the patient; and
    means, circumscribing said reservoir means, for applying pressure to said reservoir means to drive the collected fluids from said reservoir through said conduit, whereupon said reservoir means is prepared to receive and store further excess fluids from said suctioning means.

4. The closed drainage apparatus of claim 3 wherein said suctioning means comprises a resilient container which is compressible to create a suctioning force as it returns to its normal expanded condition.

5. The closed drainage apparatus of claim 4 wherein said reservoir means comprises an impervious, flexible bag.

6. The closed drainage apparatus of claim 3 wherein said suctioning means comprises a resilient bellows which produces a suctioning force as it returns to its normal expanded condition.

7. The closed drainage apparatus of claim 3 including, a one-way valve to prevent liquids and gases from flowing back from said reservoir means into said suctioning means.

8. The closed drainage apparatus of claim 3 wherein said reservoir means is provided with means for venting gases.

9. The closed drainage apparatus of claim 3 including a reflux valve for preventing reflux of liquids and gases from said suctioning means to the body and tissue cavities.

10. The closed drainage apparatus of claim 9 wherein said reflux valve comprises a duckbill valve.

* * * * *